(12) United States Patent
Smith et al.

(10) Patent No.: US 9,999,525 B2
(45) Date of Patent: Jun. 19, 2018

(54) PROSTHETIC FOOT

(71) Applicant: Ability Dynamics, LLC, Tempe, AZ (US)

(72) Inventors: Keith B. Smith, Gilbert, AZ (US); Brian Werner, Queen Creek, AZ (US)

(73) Assignee: Ability Dynamics, LLC, Tempe, AZ (US)

( * ) Notice: Subject to any disclaimer, the term of this patent is extended or adjusted under 35 U.S.C. 154(b) by 0 days. days.

(21) Appl. No.: 14/995,782

(22) Filed: Jan. 14, 2016

(65) Prior Publication Data

US 2016/0206446 A1    Jul. 21, 2016

Related U.S. Application Data

(60) Provisional application No. 62/103,649, filed on Jan. 15, 2015.

(51) Int. Cl.
*A61F 2/66*       (2006.01)

(52) U.S. Cl.
CPC .......... *A61F 2/66* (2013.01); *A61F 2002/665* (2013.01); *A61F 2002/6685* (2013.01)

(58) Field of Classification Search
CPC .. A61F 2/66; A61F 2/6607; A61F 2002/6614; A61F 2002/6678
See application file for complete search history.

(56) References Cited

U.S. PATENT DOCUMENTS

| | | |
|---|---|---|
| 4,578,082 A | 3/1986 | Sen-Jang |
| 4,822,363 A | 4/1989 | Phillips |
| 5,062,859 A | 11/1991 | Naeder |
| 5,112,356 A | 5/1992 | Harris et al. |
| 5,116,382 A | 5/1992 | Wilson et al. |
| 5,156,632 A | 10/1992 | Wellershaus |
| 5,443,522 A | 8/1995 | Hiemisch |
| 5,888,239 A | 3/1999 | Wellershaus et al. |
| 5,897,594 A | 4/1999 | Martin et al. |
| 5,944,760 A | 8/1999 | Christensen |

(Continued)

FOREIGN PATENT DOCUMENTS

| | | |
|---|---|---|
| WO | 2011133717 a1 | 10/2011 |
| WO | 2014147070 A1 | 9/2014 |

OTHER PUBLICATIONS

Moloney et al, "Parameters determining the strength and toughness of particulate filled epoxide resins," Journal of Materials Science, Feb. 1, 1987, pp. 381-393.

*Primary Examiner* — Bruce E Snow
(74) *Attorney, Agent, or Firm* — The Noblitt Group, PLLC

(57) ABSTRACT

A prosthetic foot may comprise a resilient lower member, a resilient upper member and an upper bracket. The resilient lower member may comprise a front end, a middle, and a rear end. The resilient upper member may comprise a front end and a rear end. The rear end of the upper member is coupled to the rear end of the resilient lower member and the resilient upper member is positioned over the resilient lower member. The mounting bracket may comprise a front end and a rear end. The front end is coupled to the front end of the resilient upper member and the rear end is configured to attach to the residual limb of the user. The resilient lower member and resilient upper member of the prosthetic foot fit completely within a foot shell.

18 Claims, 17 Drawing Sheets

(56) References Cited

U.S. PATENT DOCUMENTS

| | | | |
|---|---|---|---|
| 5,993,488 A * | 11/1999 | Phillips | A61F 2/66 623/49 |
| 6,077,301 A | 6/2000 | Pusch | |
| 6,099,572 A | 8/2000 | Mosler et al. | |
| 6,120,547 A | 9/2000 | Christensen | |
| 6,197,068 B1 | 3/2001 | Christensen | |
| 6,241,776 B1 | 6/2001 | Christensen | |
| 6,261,324 B1 | 7/2001 | Merlette | |
| 6,663,673 B2 | 12/2003 | Christensen | |
| 6,669,737 B2 | 12/2003 | Mosier et al. | |
| 6,702,858 B2 | 3/2004 | Christensen | |
| 6,712,860 B2 | 3/2004 | Rubie et al. | |
| 6,764,522 B1 | 7/2004 | Cehn | |
| 6,767,370 B1 | 7/2004 | Mosier et al. | |
| 6,805,717 B2 | 10/2004 | Christensen | |
| 6,852,131 B1 | 2/2005 | Chen et al. | |
| 6,875,241 B2 | 4/2005 | Christensen | |
| 6,875,242 B2 | 4/2005 | Christensen | |
| 6,911,052 B2 | 6/2005 | Christensen | |
| 6,929,665 B2 | 8/2005 | Christensen | |
| 6,942,704 B2 | 9/2005 | Sulprizio | |
| 6,966,933 B2 | 11/2005 | Christensen | |
| 7,063,727 B2 | 6/2006 | Phillips et al. | |
| 7,172,630 B2 | 2/2007 | Christensen | |
| 7,178,218 B1 | 2/2007 | Houser et al. | |
| 7,341,603 B2 | 3/2008 | Christensen | |
| 7,419,509 B2 | 9/2008 | Christensen | |
| 7,462,201 B2 | 12/2008 | Christensen | |
| 7,520,904 B2 | 4/2009 | Christensen | |
| 7,572,299 B2 | 8/2009 | Christensen | |
| 7,618,464 B2 | 11/2009 | Christensen | |
| 7,686,848 B2 | 3/2010 | Christensen | |
| 7,727,285 B2 | 6/2010 | Christensen | |
| 7,740,602 B2 | 6/2010 | Christensen | |
| 7,771,488 B2 | 8/2010 | Asgeirsson et al. | |
| 7,794,506 B2 | 9/2010 | Christensen | |
| 7,824,446 B2 | 11/2010 | Christensen et al. | |
| 7,846,213 B2 | 12/2010 | Lecomte et al. | |
| 7,951,101 B2 | 5/2011 | Pusch | |
| 7,955,399 B2 | 6/2011 | Townsend et al. | |
| 8,007,544 B2 | 8/2011 | Jonsson et al. | |
| 8,034,121 B2 | 10/2011 | Christensen | |
| 8,070,828 B2 | 12/2011 | Shannon | |
| 8,092,550 B2 | 1/2012 | McCarvill et al. | |
| 8,202,325 B2 | 6/2012 | Albrecht-Laatsch et al. | |
| 8,246,695 B2 | 8/2012 | Mosler | |
| 8,317,877 B2 | 11/2012 | Doddroe et al. | |
| 8,474,329 B2 | 7/2013 | Schulze et al. | |
| 8,500,825 B2 | 8/2013 | Christensen et al. | |
| 8,771,370 B2 | 7/2014 | Albrecht-Laatsch et al. | |
| 8,900,326 B2 | 12/2014 | Doddroe et al. | |
| 8,945,238 B2 | 2/2015 | Mosler et al. | |
| 9,161,846 B2 | 10/2015 | Mosler | |
| 9,351,853 B2 | 5/2016 | Doddroe et al. | |
| 2002/0013628 A1 * | 1/2002 | Harris | A61F 2/66 623/55 |
| 2002/0040249 A1 | 4/2002 | Phillips | |
| 2002/0188355 A1 | 12/2002 | Chen | |
| 2003/0109638 A1 | 6/2003 | Briggs et al. | |
| 2004/0225375 A1 | 11/2004 | Chen | |
| 2004/0236435 A1 | 11/2004 | Chen | |
| 2005/0033450 A1 | 2/2005 | Christensen | |
| 2005/0033451 A1 | 2/2005 | Aigner et al. | |
| 2005/0038525 A1 | 2/2005 | Doddroe et al. | |
| 2005/0203640 A1 | 9/2005 | Christensen | |
| 2005/0216098 A1 | 9/2005 | Christensen | |
| 2006/0069450 A1 | 3/2006 | McCarvill et al. | |
| 2006/0167563 A1 | 7/2006 | Johnson et al. | |
| 2006/0212131 A1 | 9/2006 | Curtis | |
| 2006/0224246 A1 | 10/2006 | Clausen | |
| 2006/0241783 A1 | 10/2006 | Christensen | |
| 2008/0033578 A1 | 2/2008 | Christensen | |
| 2008/0167730 A1 | 7/2008 | Pusch | |
| 2008/0188951 A1 | 8/2008 | Christensen et al. | |
| 2008/0228288 A1 | 9/2008 | Nelson et al. | |
| 2009/0076626 A1 | 3/2009 | Ochoa | |
| 2009/0204229 A1 | 8/2009 | Mosler et al. | |
| 2010/0004757 A1 | 1/2010 | Clausen et al. | |
| 2010/0042228 A1 | 2/2010 | Doddroe et al. | |
| 2011/0009982 A1 | 1/2011 | King et al. | |
| 2011/0029097 A1 | 2/2011 | Ochoa | |
| 2011/0197682 A1 | 8/2011 | Palmer | |
| 2011/0199101 A1 | 8/2011 | Steele | |
| 2011/0202144 A1 | 8/2011 | Palmer | |
| 2011/0208322 A1 | 8/2011 | Rifkin et al. | |
| 2011/0320012 A1 | 12/2011 | Christensen et al. | |
| 2012/0046760 A1 | 2/2012 | Nissels et al. | |
| 2012/0179274 A1 | 7/2012 | Christensen | |
| 2012/0205206 A1 | 8/2012 | Chen et al. | |
| 2012/0209406 A1 | 8/2012 | Chen et al. | |
| 2012/0271434 A1 | 10/2012 | Friesen et al. | |
| 2013/0066439 A1 | 3/2013 | Zamora et al. | |
| 2013/0173023 A1 | 7/2013 | Lecomte et al. | |
| 2013/0289742 A1 | 10/2013 | Halldorsson et al. | |
| 2014/0018938 A1 | 1/2014 | Bertels et al. | |
| 2014/0156027 A1 | 6/2014 | Smith et al. | |
| 2014/0336782 A1 | 11/2014 | Mosler et al. | |
| 2015/0134081 A1 | 5/2015 | Geiger et al. | |
| 2015/0289996 A1 | 10/2015 | Smith | |
| 2016/0158030 A1 | 6/2016 | Doddroe et al. | |

* cited by examiner

4A

4B

4C

PROSTHETIC FOOT

CROSS-REFERENCES TO RELATED APPLICATIONS

This application claims the benefit of U.S. Provisional Patent Application No. 62/103,649, filed Jan. 15, 2015, and incorporates the disclosure of such application by reference.

BACKGROUND OF THE INVENTION

Prosthetic feet are well known in the art. In use, such prosthetic feet typically do not replicate the action of a real foot and may generate "kickback" or "kickforward" reactions that increase the risk of injury to an amputee utilizing the foot. Kickback is motion created by the prosthetic foot in a backward direction during the walking cycle. Kickforward is motion created by the prosthetic foot in a forward direction during the waking cycle. Either motion may create instability for user by expanding or restricting the intended motion. Further, prosthetic feet typically generate vibrations that may travel through a user's leg and cause discomfort.

For an amputee, loosing bipedality may produce an involuntary anterior lean or shift, forcing a constant imbalance or rebalance of posture. The amputee no longer possesses voluntary muscle control on his involved side due to the severance of the primary flexor and extensor muscles. The primary anterior muscle responsible for dorsiflexion (sagittal plane motion) is the anterior tibialis. Dorsiflexion is the voluntary ankle motion that elevates the foot upwards, or towards the midline of the body. The primary posterior muscle responsible for plantarflexion is the gastro-soleus complex, which is a combination of two muscles working in conjunction: the gastrocnemius and the soleus. Plantarflexion is the voluntary ankle motion that depresses the foot downwards, or away from the midline of the body.

There are multiple types of amputations, which require prosthetic limbs. For prosthetic feet there are generally above the knee and below the knee amputations. With below the knee amputations the type of prosthetic foot required often depends on the length of the residual limb of the user. One type of below the knee amputation is known as a Syme's amputation, which is an amputation of the foot through the articulation of the ankle with removal of the malleoli of the tibia and fibula. The Syme's amputation can be one of the best amputations of the lower extremity because it creates a long residual limb and excellent end-bearing stump, which allows for a functionally satisfactory prosthesis. However, due to the length of the residual limb, there is limited space and a compact prosthetic foot is required.

SUMMARY OF THE INVENTION

An exemplary prosthetic foot may comprise a resilient lower member having a forward end and a rear end, a resilient upper member having a forward end and a rear end, wherein the rear end of the resilient upper member is connected to the rear end of the resilient lower member, and wherein the resilient upper member is positioned over the resilient lower member and directed towards the front of the prosthetic foot, and a heel member. The heel member may comprise at least one spacer coupled to, and creating space between, the rear end of the lower member and the rear end of the upper member. The prosthetic foot may comprise an upper bracket attached to the resilient upper member and configured for attachment to the residual limb of the user.

In another embodiment, an exemplary prosthetic foot may comprise a resilient lower member having a forward end and a rear end, a resilient upper member having a forward end and a rear end, wherein the rear end of the resilient upper member is connected to the rear end of the resilient lower member, and wherein the resilient upper member is positioned over the resilient lower member and directed towards the front of the prosthetic foot. The rear end of the resilient upper member may be connected to the rear end of the resilient lower member by a mechanical connection. A spacer may be coupled to, and create space between, the rear end of the lower member and the rear end of the upper member. The prosthetic foot may comprise an upper bracket attached to the resilient upper member and configured for attachment to the residual limb of the user.

BRIEF DESCRIPTION OF THE DRAWINGS

A more complete understanding of the present invention may be derived by referring to the detailed description and claims when considered in connection with the following illustrative figures. In the following figures, like reference numbers refer to similar elements and steps throughout the figures.

Figure 1:
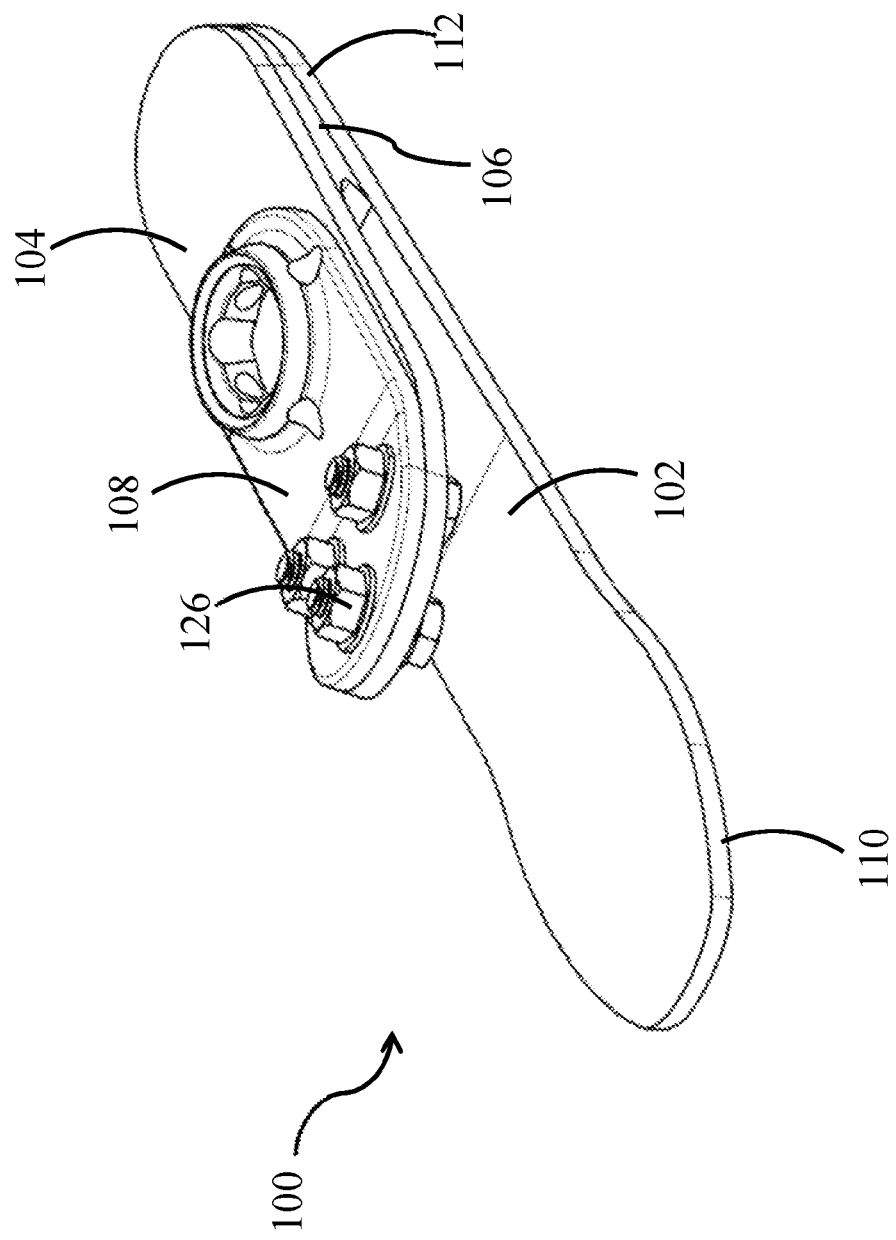
FIG. 1 is a perspective view representatively illustrating a prosthetic foot in accordance with exemplary embodiments of the present technology.

Elements and steps in the figures are illustrated for simplicity and clarity and have not necessarily been rendered according to any particular sequence. For example, steps that may be performed concurrently or in a different order are illustrated in the figures to help to improve understanding of embodiments of the present technology.

DETAILED DESCRIPTION OF EXEMPLARY EMBODIMENTS

The present technology may be described in terms of functional block components and various processing steps. Such functional blocks may be realized by any number of components configured to perform the specified functions and achieve the various results. For example, the present technology may include a prosthetic foot for above and below knee amputees. In addition, the present technology may be practiced in conjunction with any number of materials and methods of manufacture and the system described is merely one exemplary application for the technology.

Briefly, in accordance with exemplary embodiments, a prosthetic foot is illustrated which comprises a more natural motion and response of the foot occurs during movement. In particular, the movement of the exemplary prosthetic foot replicates the natural flex of a foot and supplies continuous return energy from physical inputs to a person when striding from heel to toe. The prosthetic foot also provides for a compact prosthetic foot that replicates the function and feel of a typical prosthetic foot.

In an exemplary embodiment a prosthetic foot stores energy during the gait cycle and transfers the return potential energy in order to "put a spring in your step." The gait cycle, and specifically the stance phase, includes a heel-strike phase, a mid-stance phase, and a toe-off phase. The heel-strike phase begins when the heel of the foot touches the ground, and includes the loading response on the foot. The mid-stance phase is when the foot is flat on the ground and the body's center of gravity is over the foot. The toe-off phase is the finish of the stance phase and ends when the tip of the foot is the only portion in contact with the ground, and the load is entirely on the toe.

The roll through of a prosthetic foot is defined in the gait cycle as the process from the heel-strike phase to the mid-stance phase to the toe-off phase, where the foot is no longer in contact with the ground. As the user moves through the gait cycle the tibia portion of the leg, or that section of the leg defined below the knee, rotates through in relation to the ground. If the mid-stance phase is defined as the lower leg at 90 degrees to the ground, then looking at the left side of an individual, the angle of the lower leg at the heel-strike phase may occur at approximately 65 degrees and the angle of the lower leg at the toe-off phase may occur at approximately 110 degrees. The rotation of the lower leg on the theoretical ankle is notated as tibial progression or lower leg progression during the stance phase.

For prosthetic feet there are generally above the knee and below the knee amputations. With below the knee amputations the type of prosthetic foot required often depends on the length of the residual limb of the user. One type of below the knee amputation is known as a Syme's amputation, which is an amputation of the foot through the articulation of the ankle with removal of the malleoli of the tibia and fibula. The Syme's amputation can be one of the best amputations of the lower extremity because it leaves a long residual limb with an excellent end-bearing stump to allow for a functionally satisfactory prosthesis. The advantage to a Syme's amputation is that the load bearing portion of the bottom of the tibia remains intact. Because of this, the individual can still walk on the residual limb and it can bear weight. This means the residual limb can bear weight in the bottom of the socket, or the user can walk directly on their the residual limb for limited periods such as getting up in the middle of the night without having to put on their prosthesis. Another advantage is the long residual limb allows the user a great deal of leverage in athletics. The user may put a substantial amount of load on the toe of their prosthetic device for quick movement. However, due to the length of the residual limb, there is limited space and a compact prosthetic foot is required.

Standard prosthetic feet for users having long residual limbs are very compact and typically are made utilizing high stiffness composite materials. Due to the compact nature of the foot, the resilient member or the load bearing portion of the foot must be very stiff to support the substantial amount of load that the user may place on the toe of their prosthetic device during quick movement. The stiffness of the resilient member often results in a high failure rate. Accordingly, utilizing a lower stiffness material and lengthening the composite member or members while still allowing the foot to be compact can provide more comfort and versatility to the user while also reducing the failure rate of the prosthetic foot.

Figure 2:
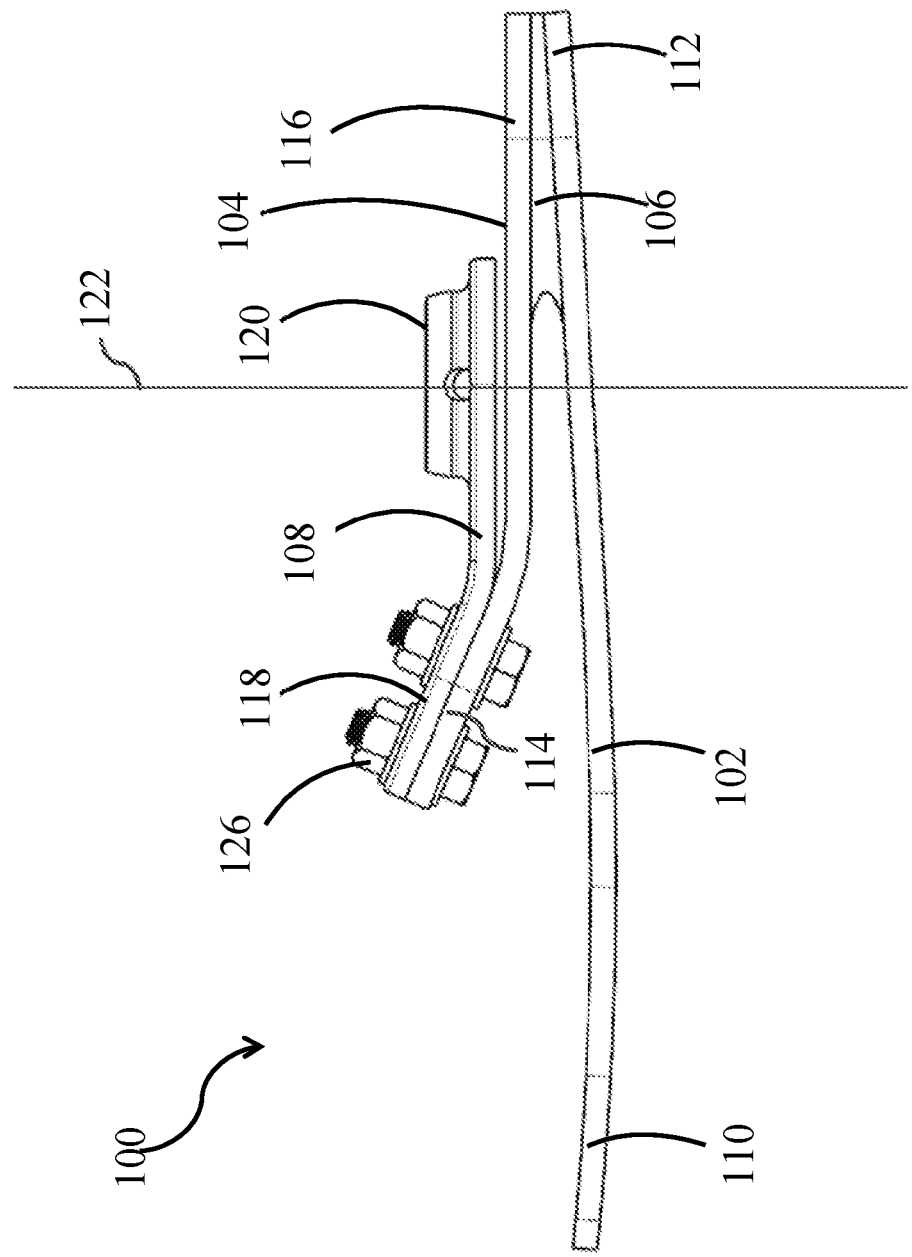
FIG. 2 is a side view representatively illustrating the prosthetic foot in accordance with exemplary embodiments of the present technology of FIG. 1.
Figures 3A, 3B, 3C:
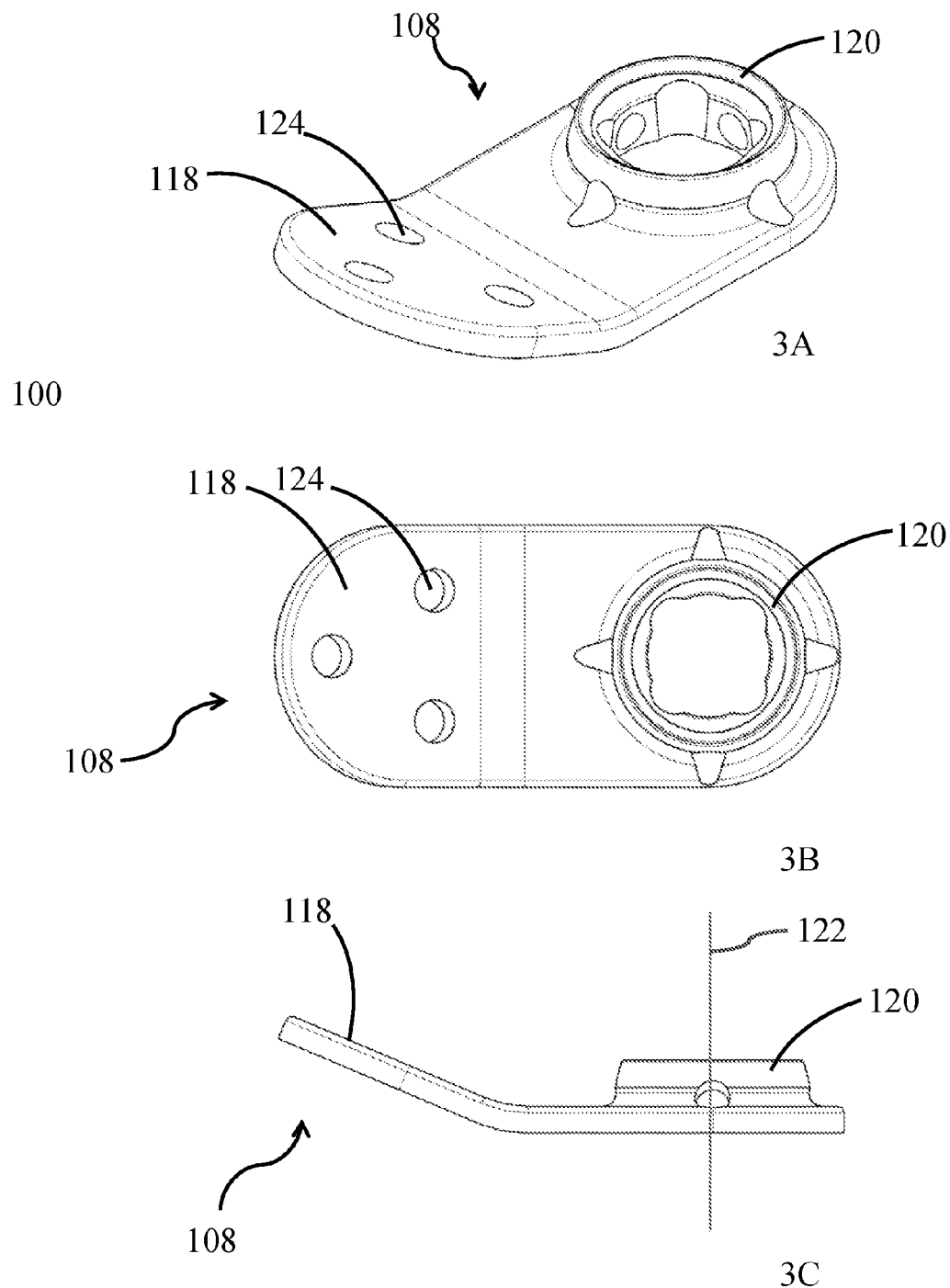
FIG. 3A-3C are a perspective view, a top view and a side view illustrating an upper bracket in accordance with exemplary embodiments of the present technology.

In accordance with various embodiments and with reference to FIGS. 1 and 2, a prosthetic foot 100 may comprise a resilient lower member 102, a resilient upper member 104, and a heel member 106. The prosthetic foot 100 may comprise an upper bracket 108 attached to the resilient upper member 104 and configured for attachment to a user's residual limb. The resilient lower member 102 may comprise a forward end 110 and a rear end 112. The resilient upper member 104 may comprise a forward end 114 and a rear end 116. Further, the rear end 116 of the resilient upper member 104 may be connected to the rear end 112 of the resilient lower member 102, while the resilient upper member 104 may be positioned over the resilient lower member 102 and directed towards the front of the prosthetic foot 100.

The resilient members 102, 104 may comprise an arc shape, which may operate like a leaf-spring to store potential energy and carry a load when in use. Orienting the resilient lower member 102, the resilient upper member 104, and the heel member 106 in this manner greatly increases the load bearing length of the resilient members in the prosthetic foot, while also allowing the prosthetic foot to remain compact. In an exemplary embodiment, a low profile prosthetic foot 100 may be below 2 inches of height.

Figure 6A:
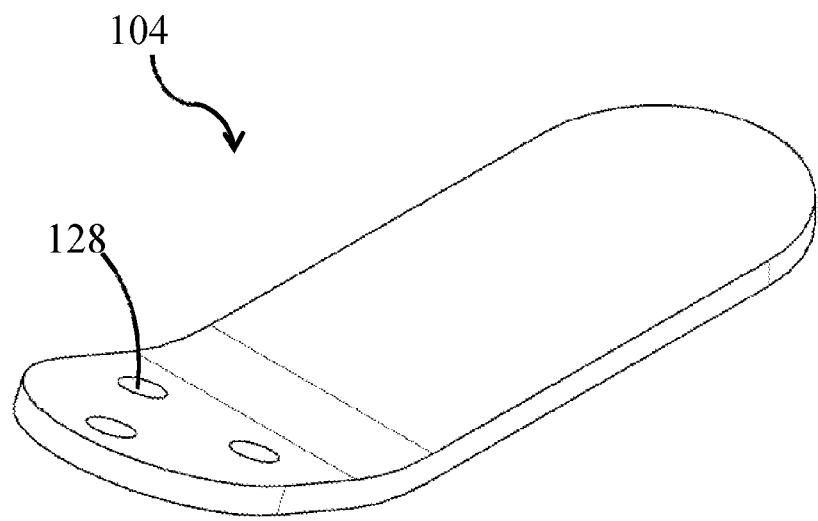
FIGS. 6A and 6B are a perspective view and a side view further illustrating a resilient upper member in accordance with exemplary embodiments of the present technology.
Figure 6B:
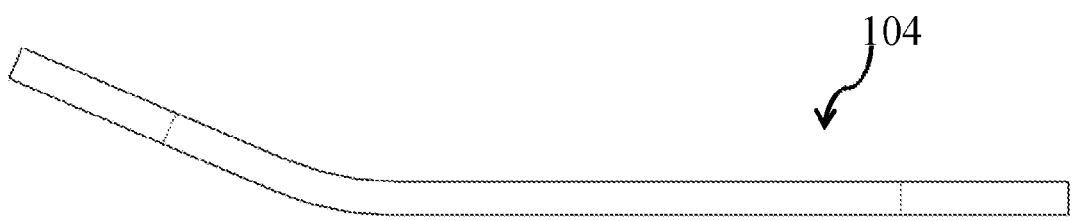

According to various embodiments and referring to FIGS. 2, 3A-3C, the prosthetic foot 100 may comprise an upper bracket 108. The upper bracket 108 may be made from Titanium (any type) or any other suitable material. Some other types of material may include mild steel, alloy steel, high strength stainless steel such as 13-8, alloy aluminum such as the 2000 and 7000 series, and any suitable composite material. The upper bracket 108 may comprise a front mounting portion 118 and an attachment portion 120, which may facilitate attachment to the residual limb of the user. The attachment portion 120 is a standard pyramid receiver used in the practice of prosthetics, for example, a Staats style attachment, which is commonly known in the prosthetic industry. The attachment portion 120 may be made from Titanium or any other suitable material. Other types of material may include mild steel; alloy steel, high strength stainless steel such as 13-8, and alloy aluminum such as the 2000 and 7000 series. The attachment portion 120 may comprise a centerline 122 that is aligned with the weight line of the user. The front mounting portion 118 may be coupled to the forward end 114 of the resilient upper member 104. In various embodiments, adhesives may be used exclusively or in combination with fasteners. The front mounting portion 118 may comprise attachment apertures 124 that extend there through to receive fasteners 126 to couple the front mounting portion 118 to the forward end 114 of the resilient upper member 104. In this embodiment, as shown in FIGS. 6A and 6B, the forward end 114 of the resilient upper member 104 contains similarly configured attachment apertures 128.

According to various embodiments and referring to FIGS. 2, 4A-4C, the elastomeric heel member 106 may contact the resilient upper member 104 and attach to an underside of the rear end 116 of the resilient upper member 104. The elastomeric heel member 106 may contact the resilient lower member 102 and attach to an upper surface of the rear end 112 of the lower member 102. The heel member 106 may act as a heel shock for absorbing force on the downward strike during the user's stride.

Figure 4A:
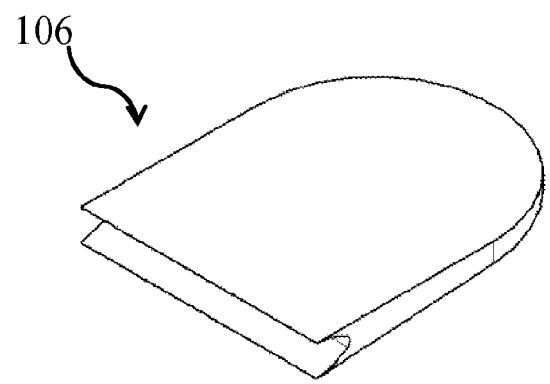
FIGS. 4A-4C are a perspective view, a top view and a side view further illustrating a heel member in accordance with exemplary embodiments of the present technology.
Figure 4B:
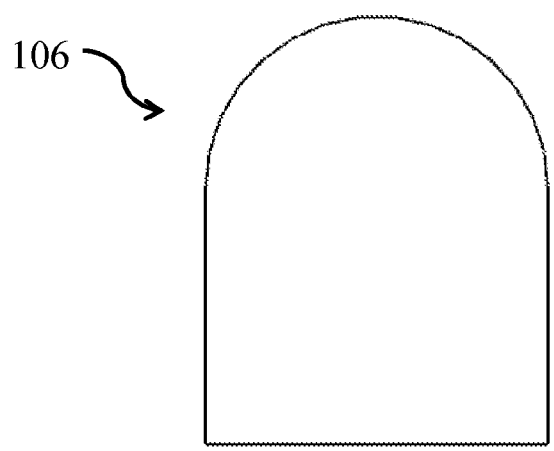
Figure 4C:

In various embodiments and as shown in FIGS. 4A-4C, the heel member 106 may comprise an elastomeric material. The elastomeric material may comprise a general elastomeric material, polyurethane, natural rubber, a synthetic rubber, or various combinations of natural and synthetic rubber. The durometer of the elastomeric material may be varied to provide additional adjustment of the prosthetic foot. The elastomeric material of the heel member 106 supports load and provides spring reaction for roll through from heel-strike phase through the mid-stance phase to the toe-off phase. The adjustable durometer of the elastomeric material allows the user to adjust the spring rate of the heel member 106 based on user needs such as activity level, compliance level, weight changes, and the like. For example, in various embodiments, the durometer of the elastomeric material can be increased for users with more heel strike force, which may be caused by additional weight of the user or dynamic activity of the user. Increased heel strike force also provides greater compression of the heel member.

In one embodiment, the elastomeric material has about 80% or greater energy return. In another embodiment, the elastomeric material has about 90% or greater energy return. The heel member 106 may be designed to behave similar to a non-linear spring, thereby allowing larger deflection during the heel strike. The progressive "spring rate" may lead to a soft heel strike but does not deflect too far as the heel member 106 compresses.

The heel member 106 may be located posterior to the vertical axis 122 of the upper bracket 108. The heel member 106 may be attached to the underside of a resilient upper member 104 in various manners. For example, the heel member 106 may be fixedly attached using adhesive or fasteners, such as bolts, screws, rivets, and the like. In another example, the heel member 106 may be detachable using fasteners or replaceable adhesive for replacement purposes.

The prosthetic foot 100 may be adjusted to accommodate a user in part by adjusting characteristics of the heel member 106. For example, in various embodiments, the durometer of heel member 106 may be increased for users with more heel strike force, which may be caused by additional weight or dynamic activity. A heavier user may be better-suited using a heel member 106 with a large cross-sectional area compared to a lighter user using a heel member 106 with a small cross-sectional area.

In various embodiments, the heel member 106 may comprise at least one spacer and an adhesive bonding the top surface of the lower member and the lower surface of the upper member. In various embodiments, the heel member 106 has approximately constant thickness. In other various embodiments, as shown in FIG. 4C, the heel member 106 may have a thickness that tapers towards the rear of the prosthetic foot 100. In other words, the heel member 106 closer to the heel may be thinner than heel member 106 closer to the toe. Further, the adhesive bonding of the heel member 106 may produce distributed stresses. Though other modulus values are contemplated, and various moduli may be used as well, a stiffer adhesive is preferred compared to a flexible adhesive.

The heel member 106 creates a space between the top surface of the resilient lower member 102 and the lower surface of the resilient upper member 104. The adhesive may be commingled with heel member 106 between the top surface of the resilient lower member 102 and heel member 106 and also between the lower surface of the resilient upper member 104 and the heel member 106. In various embodiments, the width of heel member 106 may be approximately the same width as the resilient lower member 102 and resilient upper member 104.

Moreover and with renewed reference to FIGS. 1 and 2, the resilient lower member 102, a resilient upper member 104, and heel member 106 transfer energy between themselves in a more natural, true foot manner. The loading response during the heel strike phase compresses the heel member 106 and the upper member 104, which in turn passes stored potential energy into, and causes a deflection of, a rear portion of the resilient lower member 102. Energy is transferred towards the front of the prosthetic foot 100 during the mid-stance phase. Furthermore, an upward deflection of at least one of the resilient lower member 102 and upper member 104 stores energy during the transition from the mid-stance phase to the toe-off phase of the gait cycle. When the prosthetic foot 100 is compressed, the resilient upper member 104 and the heel member 106 are compressed and displaced downwardly toward the resilient lower member 102.

With respect to the walking motion, the prosthetic foot 100 is configured to increase the surface-to-foot contact through the gait cycle. The increased surface contact allows for a smoother gait cycle, and increases stability in comparison to the typical prior art prosthetics. In exemplary embodiments, the underside of lower member has different contours that provide increased surface contact for different types of uses.

In accordance with various embodiments, the resilient lower member 102 of the prosthetic foot 100 may have various shapes depending on desired use. In one embodiment, the prosthetic foot 100 may comprise a resilient lower member 102 having a curved bottom with no inflection point. In one embodiment, the prosthetic foot 100 may comprise a resilient lower member 102 having a radius of curvature above the prosthetic foot 100. In one embodiment, the prosthetic foot 100 may comprise a resilient lower member 102 having a radius of curvature below the prosthetic foot 100. In one embodiment, the resilient lower member 102 has a constant arc due to single radius forming the partial curve of the resilient lower member 102. In one embodiment, the curve of the resilient lower member 102 may be designed as a spline of variable radii.

Figure 5A:
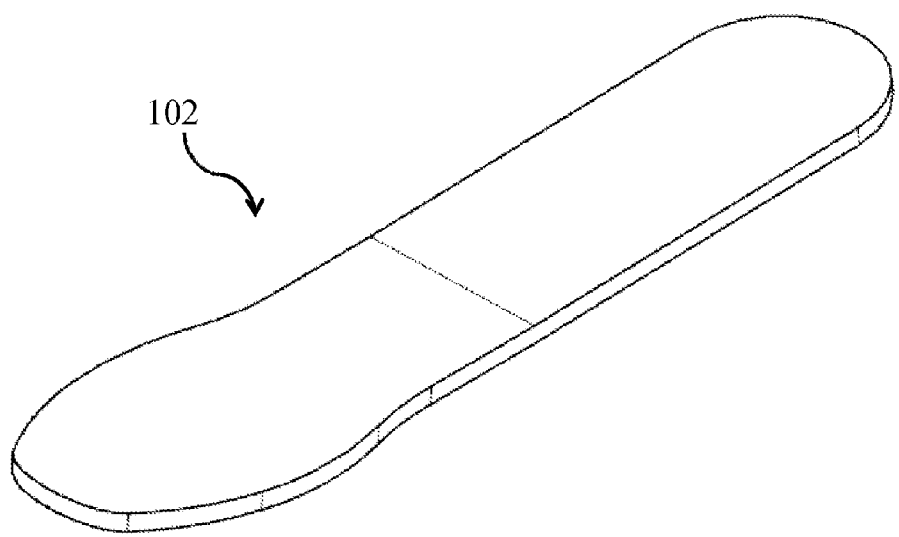
FIGS. 5A and 5B are a perspective view and a side view further illustrating a resilient lower member in accordance with exemplary embodiments of the present technology.
Figure 5B:
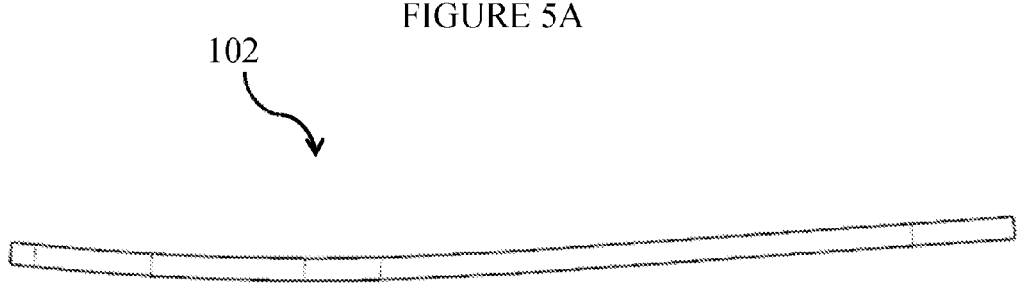

Similarly, in another embodiment as shown in FIG. 5B, the prosthetic foot 100 comprises a resilient lower member 102 having a partially curved portion in the front portion of the lower member and a substantially linear portion in the rear portion of the resilient lower member 102. The curved front portion of resilient lower member 102 may have a constant arc due to single radius forming the partial curve. In one embodiment, curved front portion of resilient lower member 102 may have a curve designed as a spline of variable radii. In accordance with various embodiments, the rear portion of resilient lower member 102 may be substantially straight and tangent to the front portion such that resilient lower member 102 does not have an inflection point. The straight rear portion and the curved front portion of resilient lower member 102 in facilitates rotation of the tibia progressing the natural rotation of the knee forward and preventing hyper-extension of the knee.

Figure 7A:
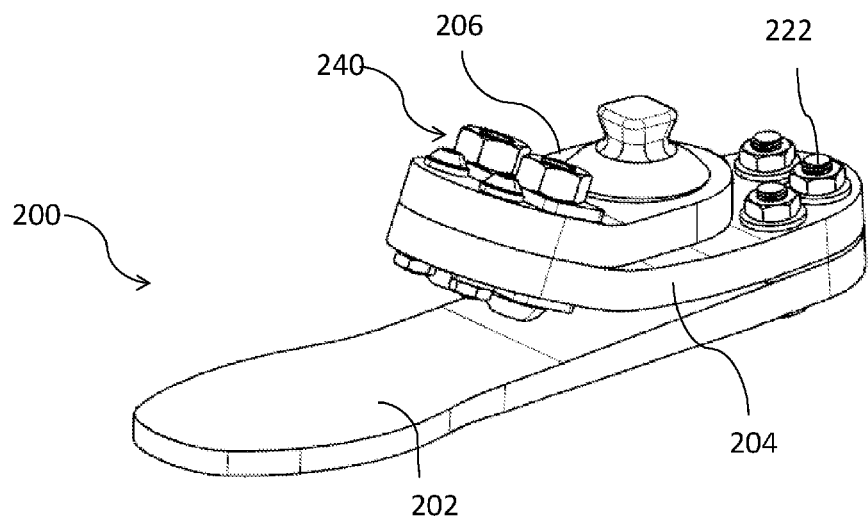
FIG. 7A is a perspective view representatively illustrating a prosthetic foot in accordance with an additional exemplary embodiment of the present technology.
Figure 7B:
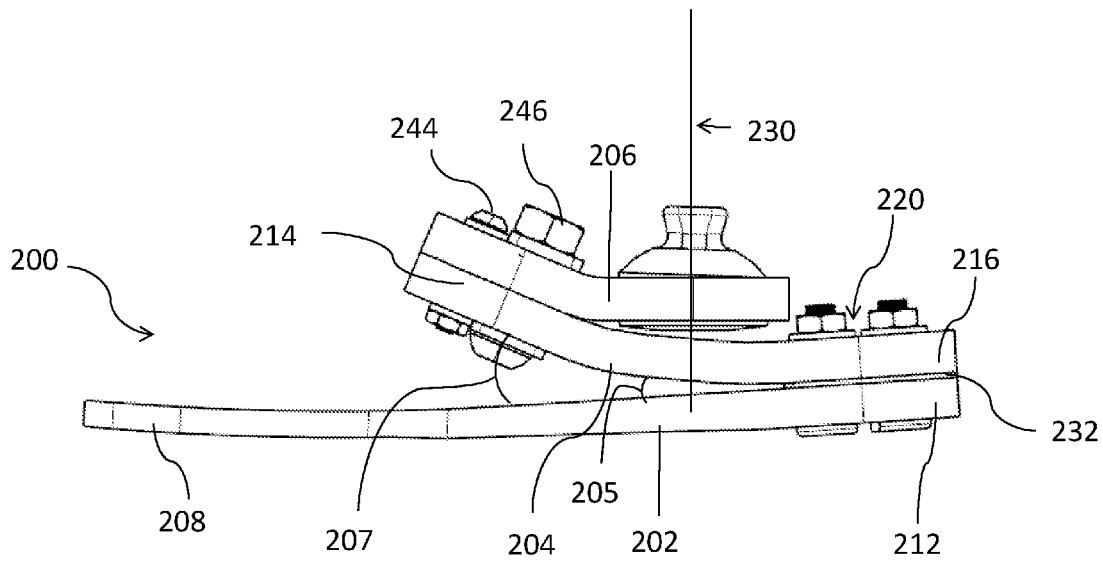
FIG. 7B is a side view representatively illustrating the prosthetic foot in accordance with exemplary embodiments of the present technology of FIG. 7A.

In accordance with exemplary embodiments and with reference to FIGS. 7A and 7B, a prosthetic foot 200 may comprise a resilient lower member 202 and a resilient upper member 204. The prosthetic foot 200 may comprise an upper bracket 206 attached to the resilient upper member 204 and configured for attachment to a user's residual limb. The upper bracket 206 may be made from Titanium or any other suitable material. Other types of material may include mild steel; alloy steel, high strength stainless steel such as 13-8, and alloy aluminum such as the 2000 and 7000 series. The resilient lower member 202 may comprise a forward end 208, a middle 210, and a rear end 212. The resilient upper member 204 may comprise a forward end 214, a middle 216, and a rear end 218. The resilient upper member 204 may be positioned over the resilient lower member 202 and directed towards the front of the prosthetic foot 200.

The resilient upper member comprises an arc length from the forward end 214 to the rear end 218 and the resilient lower member 202 comprises and arc length from the forward end 208 to the rear end 212. In one embodiment, arc length of the resilient upper member 204 from the forward end 214 to the rear end 218 is approximately 55% to 65% of the arc length of the resilient lower member 202 from the forward end 208 to the rear end 212. In one embodiment, the arc length of the resilient upper member 204 from the forward end 214 to the rear end 218 is approximately 60% of the arc length of the resilient lower member 202 from the forward end 208 to the rear end 212.

The resilient upper member 204 may be coupled to the resilient lower member 202 via a mechanical connection 220. In one embodiment, the resilient upper member 204 may be coupled to the resilient lower member 202 at an angle 205 of approximately from 3 to 5 degrees. In an exemplary embodiment, the resilient upper member 204 may be coupled to the resilient lower member 202 at an angle 205 of 3.675 degrees. In one embodiment an angle 207 of the forward end 214 of the resilient upper member 204 with respect to the resilient lower member 202 may be approximates 20-25 degrees. In an exemplary embodiment the angle 207 is 23 degrees. The resilient upper member 204 is shaped such that during use the lower surface of the resilient upper member does not contact the upper surface of the resilient lower member 202.

Figure 10A:
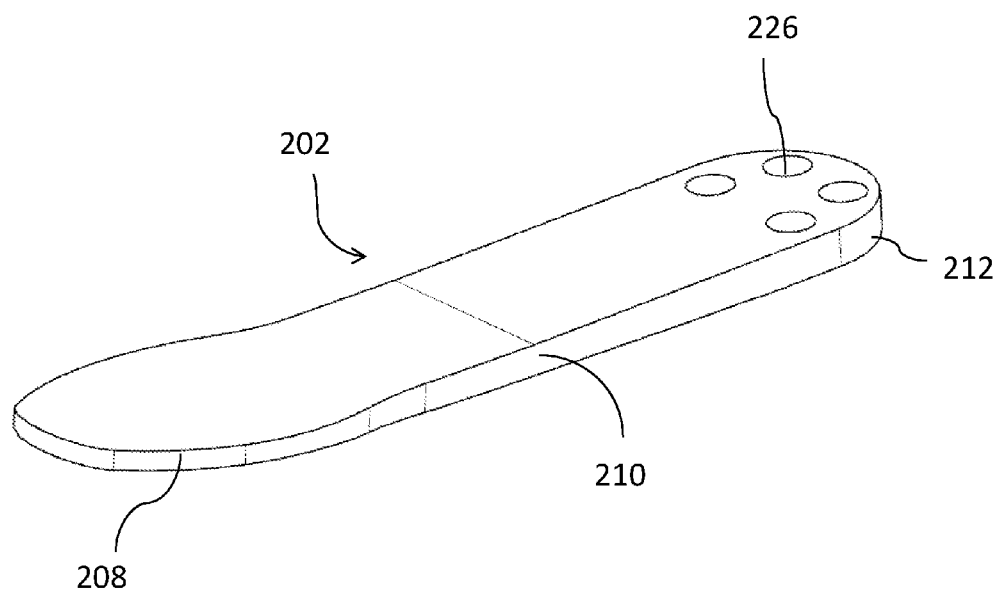
FIGS. 10A and 10B are a perspective view and a side view further illustrating a resilient lower member in accordance with an additional exemplary embodiment of the present technology.
Figure 11A:
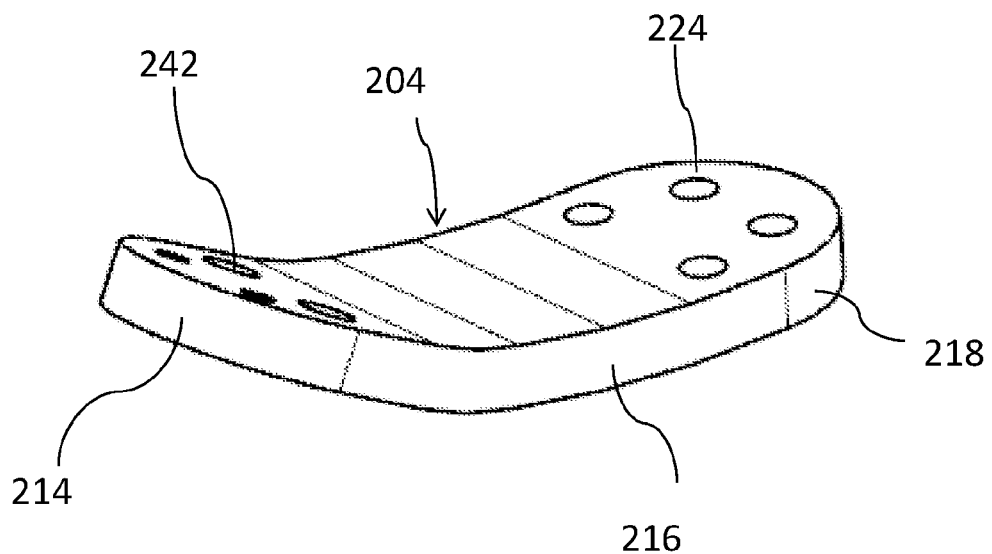
FIGS. 11A and 11B are a perspective view and a side view further illustrating a resilient upper member in accordance with an additional exemplary embodiment of the present technology.

In one embodiment, as shown in FIGS. 7A, 10A, and 11A, the rear end 218 of the resilient upper member 204 may be connected to the rear end 212 of the resilient lower member 202 via mechanical connection 220 whereby fasteners 222 are received within attachment apertures 224, 226 residing in the rear end 218 of the resilient upper member 204 and the rear end 212 of the resilient lower member 202, respectively. In one embodiment, as shown in FIGS. 7A and 7B the fasteners 222 comprise a low profile head, such as to not influence foot performance characteristics at heel strike. In one embodiment, the apertures 226 in the resilient lower member may have a counter bore such that a head of a fastener is recessed. While a bolted connection is shown any mechanical connection may be contemplated, such as screws, rivets, and the like. The bolted connection materials may comprise Titanium or any other suitable material. Other types of material may comprise mild steel, alloy steel, high strength stainless steel such as 13-8, and alloy aluminum such as the 2000 and 7000 series.

Figure 15:
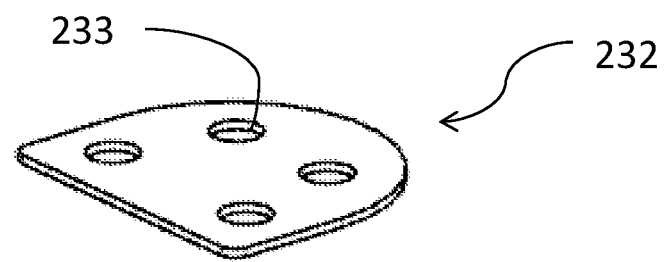
FIG. 15 is a perspective view illustrating a spacer in accordance with an exemplary embodiment of the present technology.

The mechanical connection 220 may be located posterior to the vertical axis 230 of the upper bracket 206. In one embodiment, the connection between the resilient upper member 204 and the rear end 212 of the resilient lower member 202 may comprise at least one spacer 232, shown in FIG. 15, located between the top surface of the resilient lower member 202 and the lower surface of the upper member 204. The spacer 232 may act as a heel shock for absorbing force on the downward strike during the user's stride. The spacer 232 material may comprise an elastomer, a semi-rigid, or a rigid material. In various embodiments the spacer 232 may comprise aluminum, titanium, mild steel, alloy steel, high strength stainless steel such as 13-8, and alloy aluminum such as the 2000 and 7000 series, and a composite material or any other suitable material. Varying the material of the spacer may change the function and feel of the prosthetic foot. For example, a spacer 232 comprised of stainless steel would add stiffness and reduce stress concentration in the resilient lower member 202.

The spacer 232 may comprise apertures 233 that align with apertures 224, 226. In one embodiment, an adhesive may be used to further attach the spacer 232 between the top surface of the resilient lower member 202 and the lower surface of the resilient upper member 204. In various embodiments, the spacer 232 has approximately constant thickness. In other various embodiments, the spacer 232 may have a thickness that tapers towards the rear or the front of the prosthetic foot 200. Further, the adhesive bonding of the lower member 202 and the upper member 204 may produce distributed stresses. Though other modulus values are contemplated, and various moduli may be used as well, a stiffer adhesive is preferred compared to a flexible adhesive.

The spacer 232 creates a space between the top surface of the resilient lower member 202 and the lower surface of the resilient upper member 204. An adhesive may be commingled with the spacer 232 between the top surface of the resilient lower member 202 and the lower surface of the resilient upper member 204. In various embodiments, the width of the spacer 232 may be approximately the same width as the resilient lower member 202 and resilient upper member 204. An elastomeric filler may butt up against the spacer 232 which would keep dirt, sand, or small objects from getting wedged between the resilient upper member 204 and the resilient lower member 202. Objects such and small rocks or sand could wear away the composite members eventually causing damage or failure.

Figure 8A:
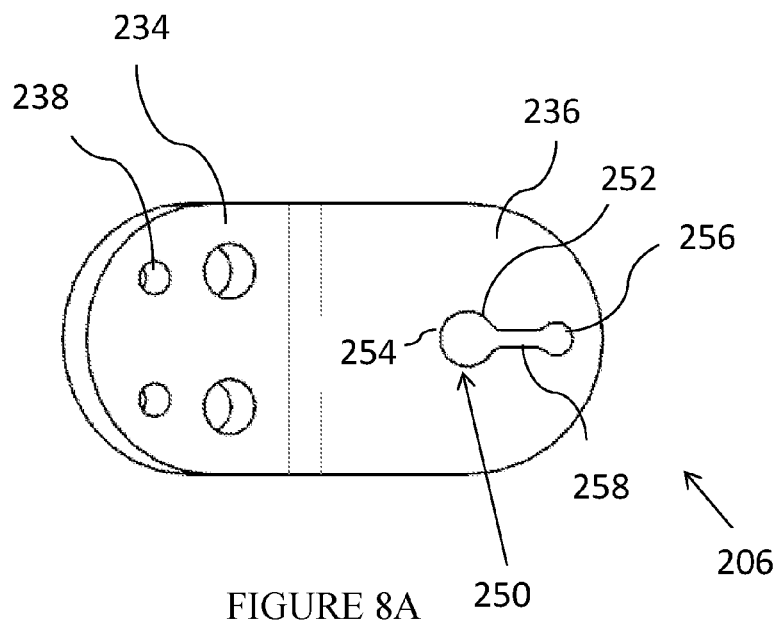
FIGS. 8A-8C are a top view, a lower view and a side view illustrating an upper bracket in accordance with an additional exemplary embodiment of the present technology.
Figure 8B:
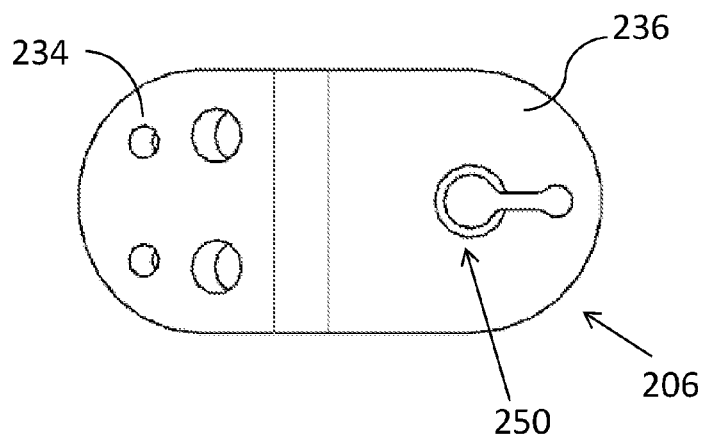
Figure 8C:
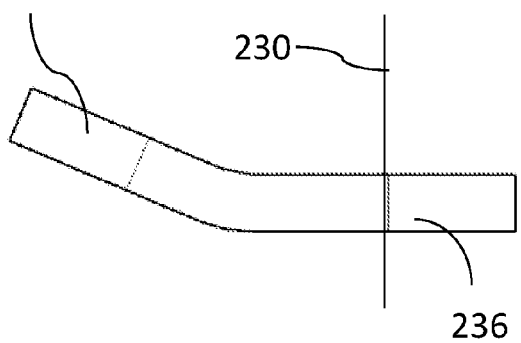
Figure 11B:
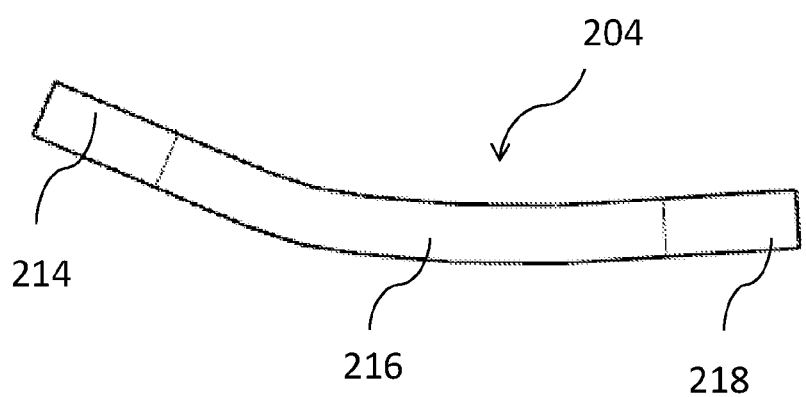

According to various embodiments and referring to FIGS. 8A-8C, the upper bracket 206 may comprise a front mounting portion 234 and an attachment portion 236, which may facilitate attachment to the residual limb of the user. The attachment portion 236 may comprise a centerline 230 that is aligned with the weight line of the user. The front mounting portion 234 may be coupled to the forward end 214 of the resilient upper member 204. The front mounting portion 234 may comprise attachment apertures 238 that extend there through to receive at least one fastener 240 to couple the front mounting portion 234 to the forward end 214 of the resilient upper member 204. The fasteners 240 can be a nut and bolt connection, a bolt/screw and threaded aperture connection, a rivet connection, and the like. Adhesives may also be used exclusively or in combination with fasteners. In this embodiment, as shown in FIGS. 11A and 11B, the forward end 214 of the resilient upper member 204 contains similarly configured attachment apertures 242.

Figure 16:
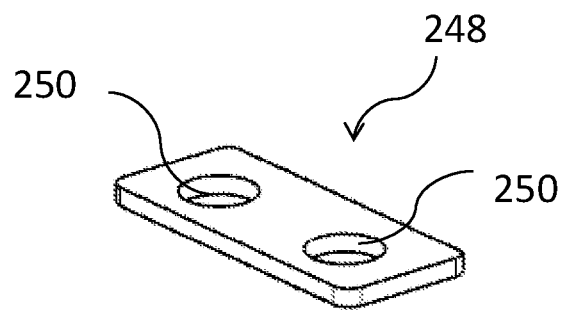
FIG. 16 is a perspective view illustrating a washer bar in accordance with an exemplary embodiment of the present technology.

In various embodiments, the fasteners 240 may comprise various sizes and configurations. As shown in FIGS. 7A and 7B, a four bolt fastener configuration is shown. In one embodiment, the fastener configuration may comprise a front pair of fasteners 244 and a rear pair of fasteners 246. The front pair of fasteners 244 and the rear pair of fasteners 246 may comprise low profile bolt heads. In some embodiments the front pair of fasteners 244 and the rear pair of fasteners 246 may be similarly sized. In one embodiment, the rear pair of fasteners 246 is sized larger than the front pair of fasteners 244 to accommodate more load. Referring again to FIGS. 7B and 16, a washer bar 248 may be used in conjunction with the rear pair of fasteners 246. The washer bar 248 may comprise a pair of apertures 250 and is designed to spread the load and reduce the stress concentration across the surface of the upper resilient member 204. While the washer bar 248 is only shown with the rear pair of fasteners 246 it is also contemplated that the front pair of fasteners 244 could also utilize the washer bar 248. Conversely, the rear pair of fasteners 246 may also utilize standard washer configurations as are shown with the front pair of fasteners 244.

The attachment portion 236 may comprise a receiving portion 250 configured for attachment of the prosthetic foot 200 to the residual limb. In one embodiment, shown in FIGS. 8A-8C, the receiving portion 250 may comprise an aperture 252 having a pair of holes 254, 256, spaced apart by a channel 258. In one embodiment, shown in 9A-9C, the receiving portion 250 may comprise a generally rectangular aperture 260.

Figure 12A:
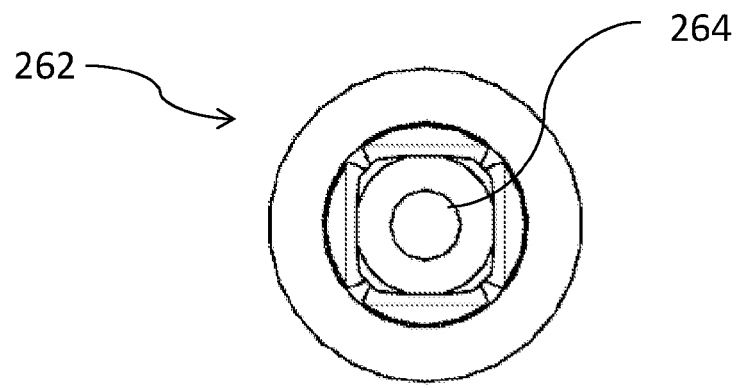
FIGS. 12A-12C are a top view, a side view, and a bottom view illustrating a limb connector in accordance with an exemplary embodiment of the present technology.
Figure 12B:
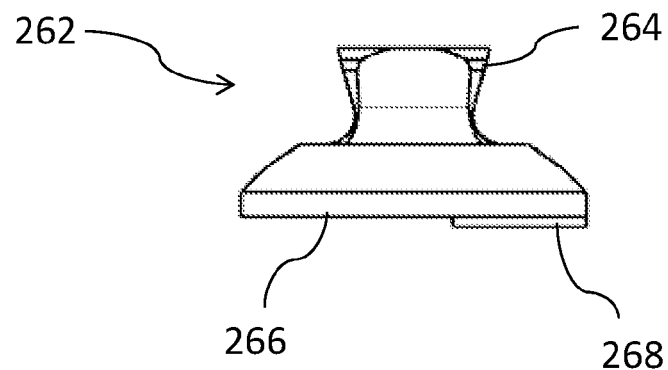
Figure 12C:
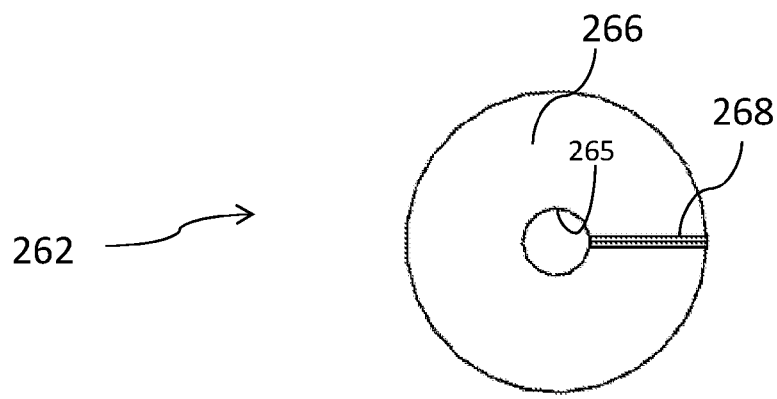
Figure 14A:
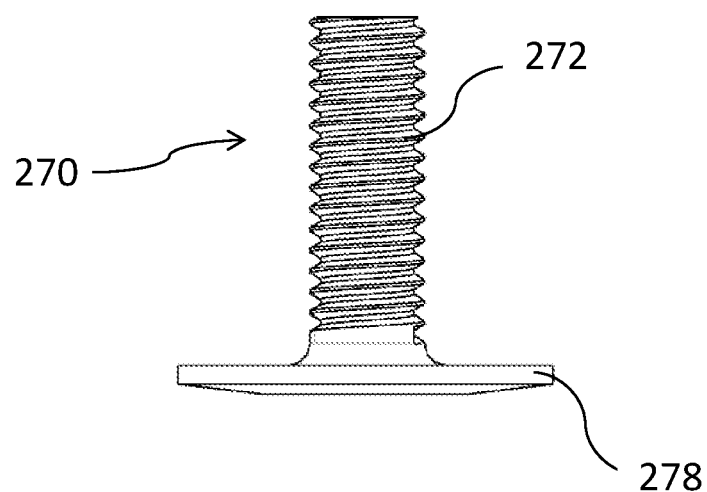
FIGS. 14A and 14B are a side view and a top view illustrating a pyramid connector in accordance with an exemplary embodiment of the present technology.
Figure 14B:
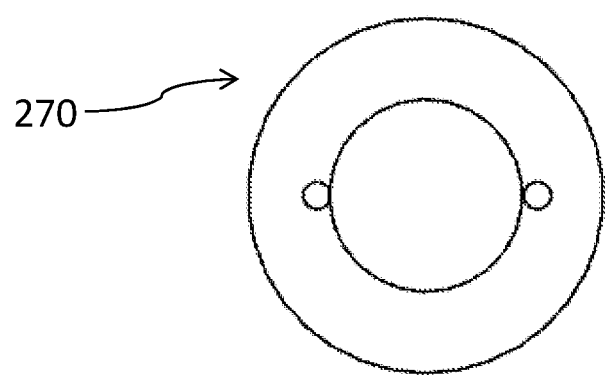

The receiving portions 250 are configured to receive limb connectors 262, which are used to connect to the standard Staats type connection in the prosthetic industry. In one embodiment, shown in FIGS. 12A-12C, a limb connector 262 may comprise a pyramid connector 264 with an internally threaded aperture 265. In one embodiment, the limb connector 262 may comprise a mounting surface 266 with a protruding wedge 268. The limb connector 262 may be coupled to the upper bracket 206 shown in FIGS. 8A-8C by placing the protruding wedge 268 within the channel 258. The mounting surface 266 would rest on the upper surface of the attachment portion 236. A connector 270, shown in FIGS. 14A and 14B may be used to couple the limb connector 262 to the upper bracket 206, shown in FIGS. 8A-8C. The connector 270 may comprise a threaded shaft 272, which is received in the internally threaded aperture 265 of the pyramid connector.

Figure 9A:
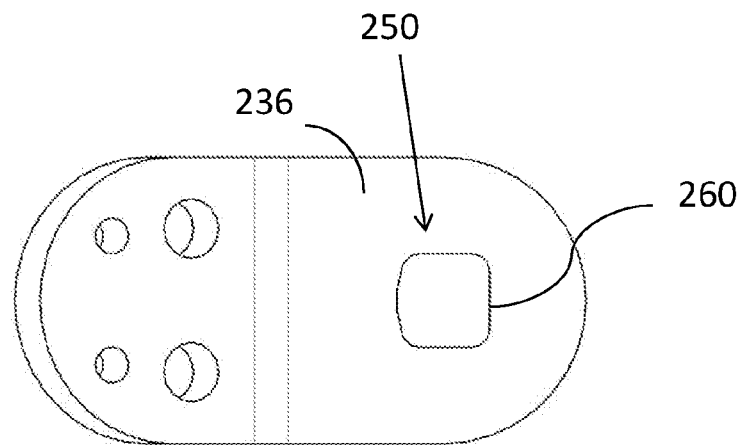
FIGS. 9A-9C are a top view, a lower view and a side view illustrating an upper bracket in accordance with an additional exemplary embodiment of the present technology.
Figure 9B:
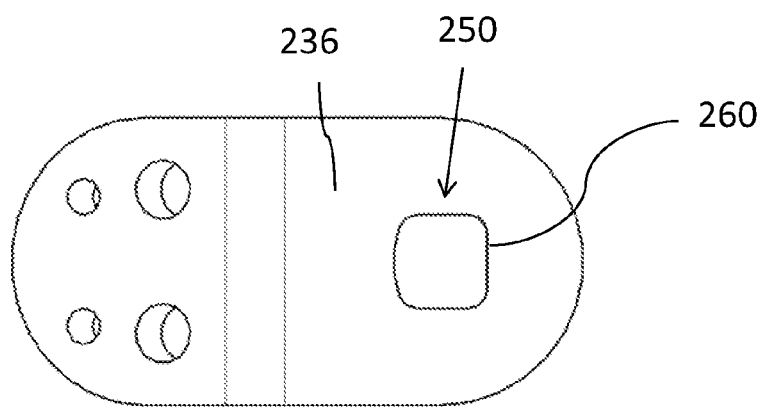
Figure 9C:
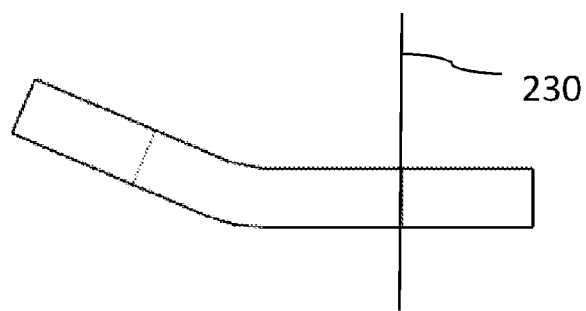
Figure 13A:
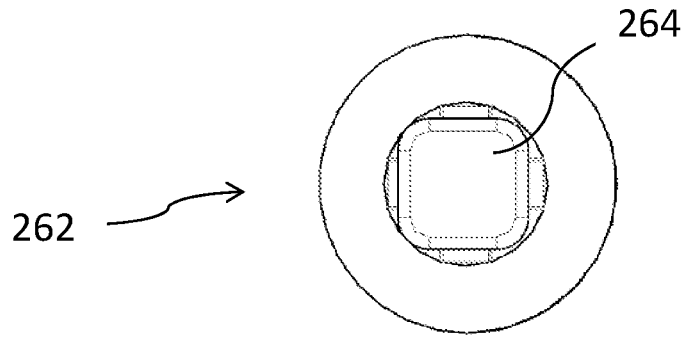
FIGS. 13A-13C are a top view, a side view, and a bottom view illustrating a limb connector in accordance with an additional exemplary embodiment of the present technology.
Figure 13B:
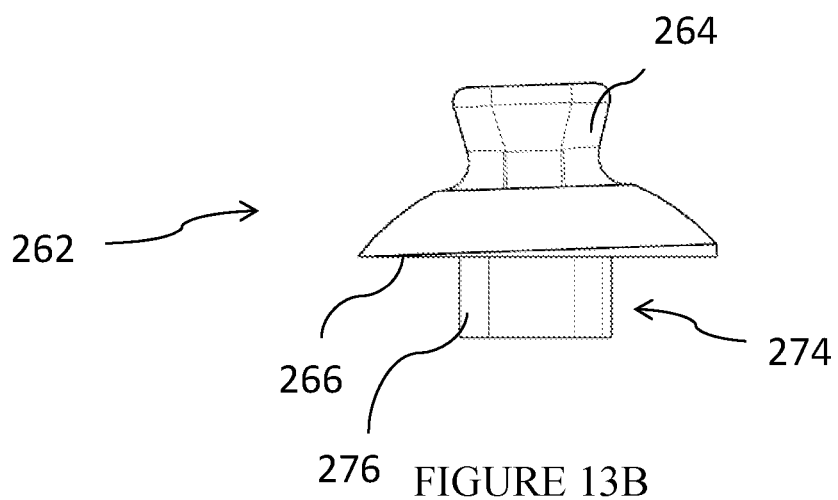
Figure 13C:
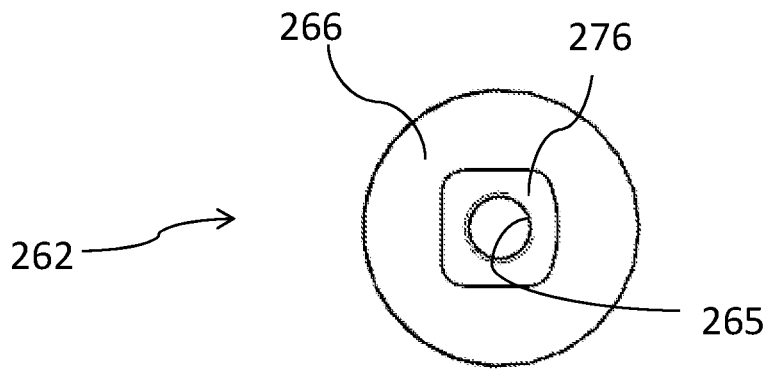

In another embodiment, shown in FIGS. 13A-C, the limb connector 262 may comprise a mounting surface 266 with a mating portion 274. In one embodiment, the mating portion 274 may comprise a protrusion 276 with a generally rectangular shape. The limb connector 262 may be coupled to the upper bracket 206, shown in FIGS. 9A-9C, by placing the mating portion 274 within the aperture 260 in the receiving portion 250. The mounting surface 266 would rest on the upper surface of the attachment portion 236. A connector 270, shown in FIGS. 14A and 14B may be used to couple the limb connector 262 to the upper bracket 206 shown in FIGS. 9A-9C. The threaded shaft 272 of the connector 270 is received in the internally threaded aperture 265 of the limb connector 262. The connector 270 may comprise a low-profile head 278, which resides on the lower surface of the attachment portion 236.

Figure 17A:
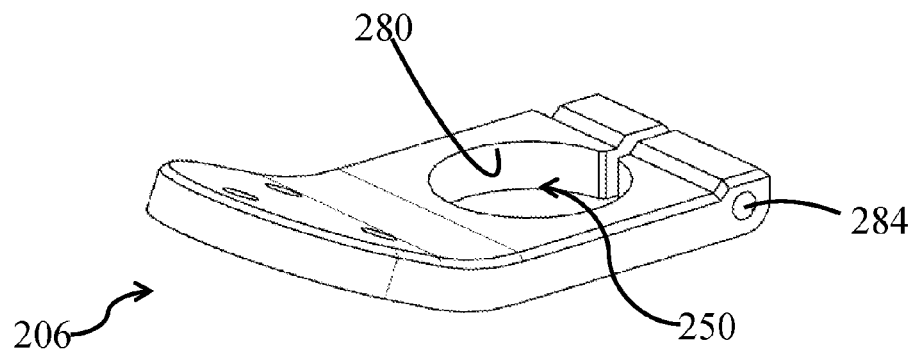
FIGS. 17A-17C are a perspective view, a top view, and a side view further illustrating an upper bracket in accordance with an additional exemplary embodiment of the present technology.
Figure 17B:
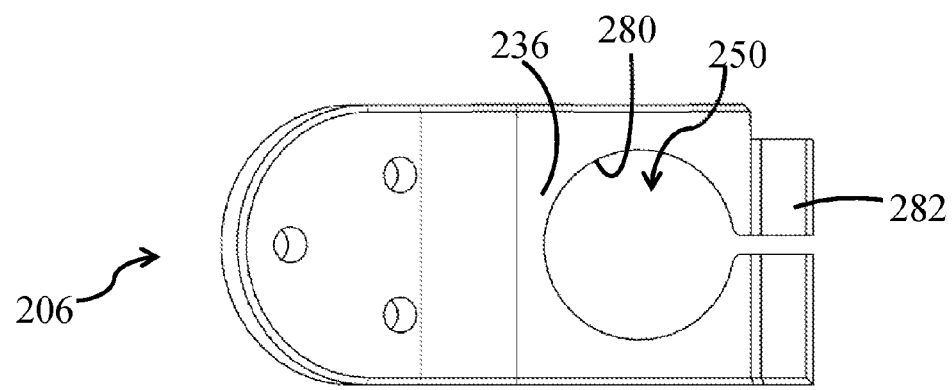
Figure 17C:
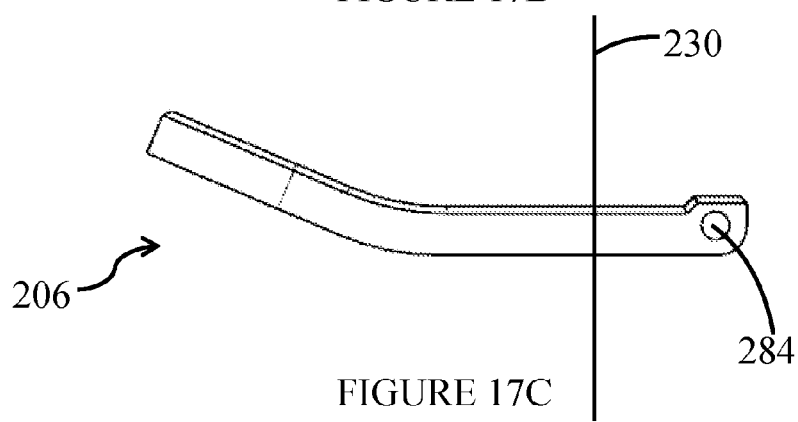

In another embodiment, shown in FIGS. 17A-17C the attachment portion 236 may comprise a receiving portion 250 with an internally threaded channel 280, which may receive a male portion of the residual limb attachment member (not shown). The threaded portion is a standard threaded configuration that may accommodate a threaded male pyramid, or a threaded female adapter that is used for standard Staats type connection in the prosthetic industry. The attachment portion 236 may comprise a clamp 282 configured to further assist attachment of the upper bracket 206 to the residual limb (not shown). The clamp 282 may comprise an internal collar 284 which receives a fastener (not shown). The collar 284 may be internally threaded to receive a bolt or unthreaded to receive a bolt and nut configuration.

Figure 18A:
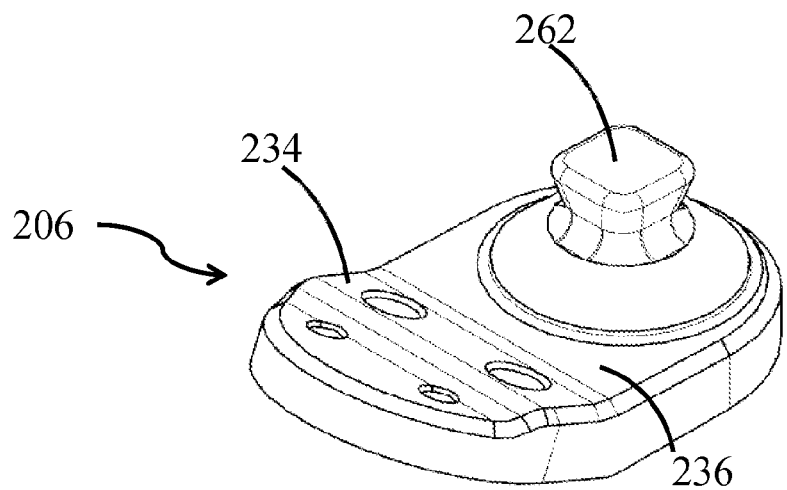
FIGS. 18A-18C are a perspective view, a side view and a bottom view illustrating an upper bracket with an integral limb connector in accordance with an additional exemplary embodiment of the present technology.
Figure 18B:
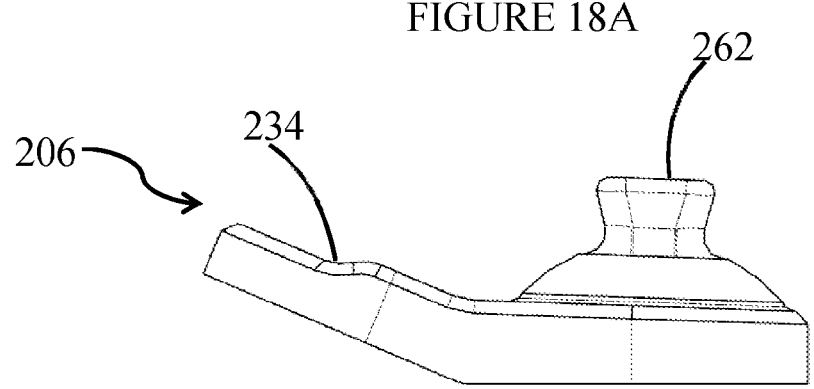
Figure 18C:
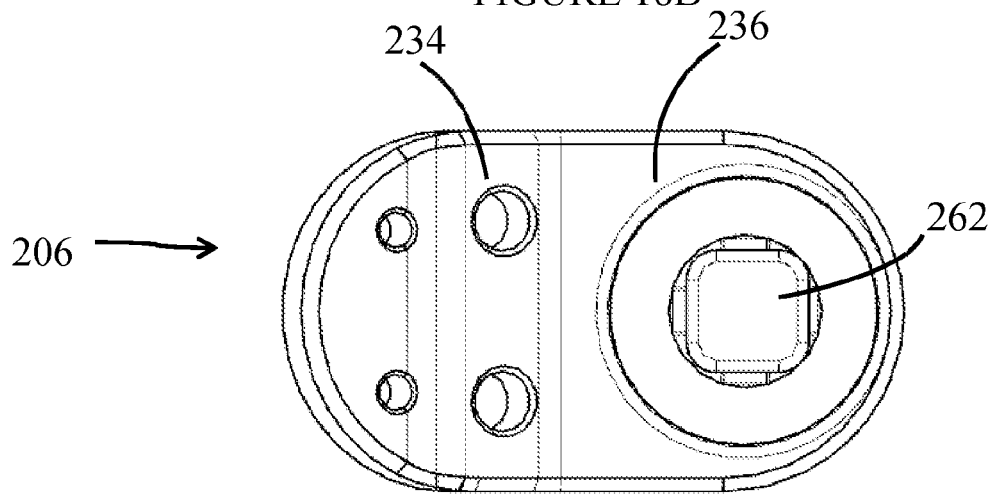

In another embodiment, shown in FIGS. 18A-C, the upper bracket 206 may comprise a front mounting portion 234 and an attachment portion 236 with an integral limb connector 262, which may facilitate attachment to the residual limb of the user by an integral limb connector 262. The upper bracket 206 may comprise an integral limb connector 262 with a standard Staats type connection in the prosthetic industry.

The resilient members 202, 204 may comprise an arc shape, which may operate like a leaf-spring to store potential energy and carry a load when in use. Orienting the resilient lower member 202 and the resilient upper member 204 in this manner greatly increases the load bearing length of the resilient members in the prosthetic foot 200, while also allowing the prosthetic foot 200 to remain compact. In an exemplary embodiment, the prosthetic foot 200 may comprise a height 286 of at least 2 inches or below. The height 286 of the prosthetic foot 200 is measured from a midpoint 263 on the limb connector 262 to the lower surface of the resilient lower member 202. The height 286 of the prosthetic foot 200 is configured to fit within the foot shell, which will be inserted into a user's shoe.

For a below the knee amputations the type of prosthetic foot required often depends on the length of the residual limb of the user. One type of below the knee amputation is known as a Syme's amputation, which is an amputation of the foot through the articulation of the ankle with removal of the malleoli of the tibia and fibula. The Syme's amputation can be one of the best amputations of the lower extremity because it creates a long residual limb and excellent end-bearing stump, which allows for a functionally satisfactory prosthesis. The long residual limb of a user can provide for a restricted height of prosthesis. Thus, the height 286 and compact nature of the prosthetic foot 200 allows the user having a long residual limb to use a prosthesis mimic the natural gate and transfer energy in a natural, true foot manner.

Moreover and with renewed reference to FIGS. 7A and 7B, the resilient lower member 202 and the resilient upper member 204 transfer energy between themselves via the mechanical connection 220 in a natural, true foot manner. The loading response during the heel strike phase causes a deflection of, a rear portion of the resilient member 202. Energy is transferred towards the front of prosthetic foot 200 during the mid-stance phase. Furthermore, an upward deflection of at least one of the resilient lower member 202 and upper member 204 stores energy during the transition from the mid-stance phase to the toe-off phase of the gait cycle. When prosthetic foot 200 is compressed, the resilient upper member 204 is compressed and displaced upwardly toward the upper bracket 206. During the gait cycle, stored energy is released from the heel as the user rolls from heel strike to midstance returning the potential energy stored in the resilient upper member 204. As the user rolls through toe off, the potential energy stored in resilient members 202 and 204 is released to assist in the motion of toe off.

With respect to the walking motion, the prosthetic foot is configured to increase the continuous line of surface-to-foot contact through the gait cycle. The increased surface contact allows for a smoother gait cycle, and increases stability in comparison to the typical prior art prosthetics. In exemplary embodiments, the underside of lower member has different contours that remain in contact with the ground through the gait cycle continuously to provide increased surface contact for different types of uses.

In accordance with various embodiments, the resilient lower member 202 and the resilient upper member 204 of the prosthetic foot 200 may have various shapes depending on desired use. In one embodiment, the prosthetic foot 200 may comprise a resilient lower member 202 having a curved bottom with no inflection point. In one embodiment, the prosthetic foot 200 may comprise a resilient upper member 204 having a curved bottom with no inflection point. In one embodiment, the prosthetic foot 200 may comprise a resilient lower member 202 having a radius of curvature above the prosthetic foot 200. In one embodiment, the prosthetic foot 200 may comprise a resilient upper member 204 having a radius of curvature above the prosthetic foot 200. In one embodiment, the prosthetic foot 200 may comprise a resilient lower member 202 having a radius of curvature below the prosthetic foot 200. In one embodiment, the resilient lower member 202 has a constant arc due to single radius forming the partial curve of the resilient lower member 202. In one embodiment, the resilient upper member 204 has a constant arc due to single radius forming the partial curve of the resilient upper member 204. In one embodiment, the curve of the resilient lower member 202 may be designed as a spline of variable radii.

In one embodiment, the prosthetic foot 200 comprises a resilient upper member 204 having a partially curved portion from the forward end 214 to the rear end 218 of the resilient upper member 204. In one embodiment, the prosthetic foot 200 comprises a resilient upper member 204 having a substantially linear portion from the forward end 214 to the middle 216 and a partially curved portion from the middle 216 to the rear end 218 of the resilient upper member 204. In one embodiment, the prosthetic foot 200 comprises a resilient upper member 204 having a substantially linear portion from the forward end 214 to the middle 216 and a substantially linear portion from the middle 216 to the rear end 218 of the resilient upper member 204 with a slight bend at an obtuse angle at approximately the middle 216.

In one embodiment, the prosthetic foot 200 comprises a resilient lower member 202 having a partially curved portion from the forward end 208 to the rear end of the resilient lower member 202. In one embodiment, the prosthetic foot 200 comprises a resilient lower member 202 having a substantially linear portion from the forward end 208 to the middle 210 and a partially curved portion from the middle 210 to the rear end of the resilient lower member 202. In one embodiment, the prosthetic foot 200 comprises a resilient lower member 202 having a substantially linear portion from the forward end 208 to the middle 210 and a substantially linear portion from the middle 210 to the rear end of the resilient lower member 202 with a slight bend at an obtuse angle at approximately the middle.

Figure 10B:
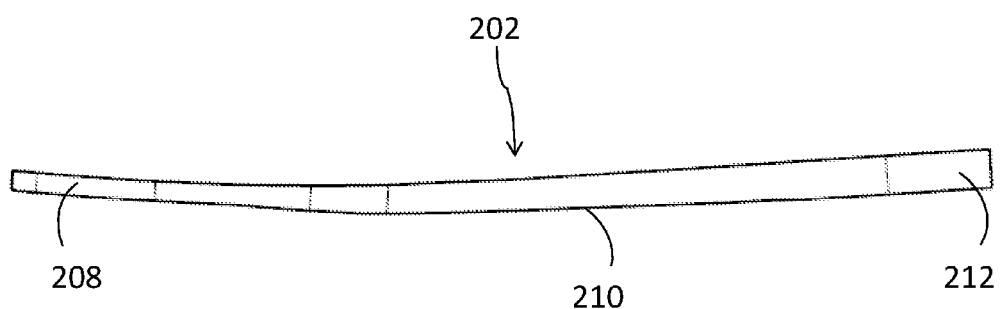

Similarly, in another embodiment as shown in FIG. 10B, the prosthetic foot 200 comprises a resilient lower member 202 having a partially curved portion from the forward end 208 to the middle 210 and a substantially linear portion from the middle 210 to the rear end 212 of the resilient lower member 202. The curved front portion of resilient lower member 202 may have a constant arc due to single radius forming the partial curve. In one embodiment, curved front portion of resilient lower member 202 may have a curve designed as a spline of variable radii. In accordance with various embodiments, the rear portion of resilient lower member 202 may be substantially straight and tangent to the front portion such that resilient lower member 202 does not have an inflection point. The substantially straight rear portion and the curved front portion of resilient lower member 202 facilitates rotation of the tibia progressing the natural rotation of the knee forward and preventing hyper-extension of the knee.

The roll through of a prosthetic foot is defined in the gait cycle as the process from the heel-strike phase to the mid-stance phase to the toe-off phase, where the foot is no longer in contact with the ground. As the user moves through the gait cycle the tibia portion of the leg, or that section of the leg defined below the knee, rotates through in relation to the ground. The rotation of the lower leg on the theoretical ankle is notated as tibial progression or lower leg progression during the stance phase.

During the gait cycle modifying the design variables of the resilient upper member 204 and resilient lower member 202 of the prosthetic foot 200 will have the effect of modifying the moment acting at the ankle and thus the tibial progression moment the user experiences. Modifying the design variables will also affect the ground forces on the user as they are transferred from prosthetic foot to the leg of the user.

The prosthetic foot 200 can be adjusted to accommodate a user in part by adjusting characteristics of the spacer 232 between the resilient upper member 204 and resilient lower member 202. For example, in various embodiments, the durometer of the spacer 232 can be increased for users with more heel strike force, which may be caused by additional weight or dynamic activity. A heavier user may be better-suited using a spacer 232 with a large cross-sectional area compared to a lighter user using a spacer 232 with a small cross-sectional area. Additionally, a heavier user may require a material, such as, steel, titanium, composite and the like.

The resilient lower member 202 and the resilient upper member 204 transfer energy between themselves via the mechanical connection 220 in a natural, true foot manner. When prosthetic foot 200 is compressed, the resilient lower member 202 and the resilient upper member 204 are compressed and displaced upwardly.

In accordance with an exemplary embodiment, the resilient lower member 202 and the resilient upper member 204 may be made of glass fiber composite, carbon fiber or other fibers. The prosthetic foot 200 can be adjusted to accommodate a user in part by adjusting characteristics of the resilient lower member 202 and the resilient upper member 204. The glass fiber composite may be a glass reinforced unidirectional fiber composite. In one embodiment, the fiber composite material is made of multiple layers of unidirectional fibers and resin to produce a strong and flexible material. The fibers may be glass fibers or carbon fibers. Specifically, layers of fiber are impregnated with the resin, and a glass reinforcement layer may be positioned between at least two fiber layers. Typically, several layers of the unidirectional fibers or tape are layered together to achieve the desired strength and flexibility. Further, in various embodiments the layers of unidirectional fibers or tape may be oriented at various angles.

The technology has been described with reference to specific exemplary embodiments. Various modifications and changes, however, may be made without departing from the scope of the present technology. The description and figures are to be regarded in an illustrative manner, rather than a restrictive one and all such modifications are intended to be included within the scope of the present technology. Accordingly, the scope of the technology should be determined by the generic embodiments described and their legal equivalents rather than by merely the specific examples described above. For example, the steps recited in any method or process embodiment may be executed in any order, unless otherwise expressly specified, and are not limited to the explicit order presented in the specific examples. Additionally, the components and/or elements recited in any apparatus embodiment may be assembled or otherwise operationally configured in a variety of permutations to produce substantially the same result as the present technology and are accordingly not limited to the specific configuration recited in the specific examples.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present technology, in addition to those not specifically recited, may be varied or otherwise particularly adapted to specific environments, manufacturing specifications, design parameters or other operating requirements without departing from the general principles of the same.

The present technology has been described above with reference to a preferred embodiment. However, changes and modifications may be made to the preferred embodiment without departing from the scope of the present technology. These and other changes or modifications are intended to be included within the scope of the present technology, as expressed in the following claims.

The invention claimed is:

1. A prosthetic foot for use within a foot shell, comprising:
   a resilient lower member comprising a front end, a middle, and a rear end, and having no inflection point, wherein a radius of curvature from the front end to the middle is above an upper surface of the resilient lower member in an unloaded state and the resilient lower member is straight from the middle to the rear end in the unloaded state;
   a resilient upper member comprising a front end and a rear end, wherein the rear end is coupled to the rear end of the resilient lower member, and wherein the resilient upper member is positioned over the resilient lower member, and wherein a lower surface of the front end of the resilient upper member is spaced apart from the upper surface of the middle of the resilient lower member; and
   a mounting bracket comprising a front end and rear end, wherein the front end is coupled to the front end of the resilient upper member,
   wherein the resilient lower member and the resilient upper member are capable of fitting completely within the foot shell.

2. The prosthetic foot of claim 1, wherein the radius of curvature from the front end to the rear end of the resilient lower member is above the lower member.

3. The prosthetic foot of claim 1, wherein the radius of curvature from the middle to the rear end of the resilient upper member is above an upper surface of the resilient upper member.

4. The prosthetic foot of claim 1, wherein the radius of curvature from the front end to the rear end of the resilient upper member is above an upper surface of the resilient upper member.

5. The prosthetic foot of claim 1, wherein the resilient upper member is coupled to the resilient lower member by a bolted connection.

6. The prosthetic foot of claim 1, wherein the resilient upper member is coupled to the mounting bracket by a bolted connection.

7. The prosthetic foot of claim 1, wherein the rear end of the mounting bracket comprises a receiving portion configured to receive a prosthetic limb connector.

8. The prosthetic foot of claim 1, wherein the mounting bracket comprises an integral prosthetic limb connector.

9. The prosthetic foot of claim 1, wherein the middle of the resilient upper member is located aft of the middle of the resilient lower member.

10. The prosthetic foot of claim 1, wherein the arc length of the resilient upper member is approximately 60% the arc length of the resilient lower member.

11. The prosthetic foot of claim 1, wherein an angle between the resilient upper member and the resilient lower member is less than 5 degrees.

12. A prosthetic foot for use within a foot shell, comprising:
    a resilient lower member comprising a front end, a middle, and a rear end, and having no inflection point, wherein a radius of curvature from the front end to the middle is above an upper surface of the resilient lower member in an unloaded state and the resilient lower member is straight from the middle to the rear end in the unloaded state;
a resilient upper member comprising a front end and a rear end, wherein the rear end is coupled to the rear end of the resilient lower member, wherein the resilient upper member is positioned over the resilient lower member, and wherein a lower surface of the front end of the resilient upper member is spaced apart from the upper surface of the middle of the resilient lower member; and
a mounting bracket comprising a front end and rear end, wherein the front end is coupled to the front end of the resilient upper member,
wherein the resilient lower member and the resilient upper member are capable of fitting completely within a foot shell.

13. The prosthetic foot of claim 12, wherein the mounting bracket comprises an integral prosthetic limb connector.

14. The prosthetic foot of claim 12, wherein the radius of curvature from the front end to the rear end of the resilient upper member is above an upper surface of the upper member.

15. The prosthetic foot of claim 12, wherein the middle of the resilient upper member is located aft of the middle of the resilient lower member.

16. The prosthetic foot of claim 12, wherein an arc length of an upper surface of the resilient upper member is approximately 60% an arc length of the upper surface of the resilient lower member.

17. The prosthetic foot of claim 12, wherein an angle between the resilient upper member and the resilient lower member is less than 5 degrees.

18. A prosthetic foot for use within a foot shell, comprising:
a resilient lower member comprising a front end, a middle, and a rear end, and having no inflection point, wherein the radius of curvature from the front end to the middle is above an upper surface of the resilient lower member in an unloaded state and the resilient lower member is straight from the middle to the rear end in the unloaded state; and
a resilient upper member comprising a front end and a rear end, wherein the rear end is coupled to the rear end of the resilient lower member, and wherein the resilient upper member is positioned over the resilient lower member, and wherein a lower surface of the front end of the resilient upper member is spaced apart from the upper surface of the middle of the resilient lower member;
wherein the resilient lower member and the resilient upper member are capable of fitting completely within a foot shell.

* * * * *